United States Patent [19]

Kang et al.

[11] 4,342,866

[45] Aug. 3, 1982

[54] HETEROPOLYSACCHARIDE S-130

[75] Inventors: Kenneth S. Kang, LaJolla; George T. Veeder, San Diego, both of Calif.

[73] Assignee: Merck & Co., Inc., Rahway, N.J.

[21] Appl. No.: 256,632

[22] Filed: Apr. 23, 1981

Related U.S. Application Data

[63] Continuation-in-part of Ser. No. 73,573, Sep. 7, 1979, abandoned.

[51] Int. Cl.$^3$ .................... C07H 1/00; C08B 37/00
[52] U.S. Cl. .................... 536/119; 252/8.5 C; 252/8.5 M; 252/8.55 D; 252/352; 435/72; 536/1; 536/114
[58] Field of Search .................... 536/1, 119

[56] References Cited

U.S. PATENT DOCUMENTS

| | | | |
|---|---|---|---|
| 3,020,206 | 2/1962 | Patton et al. | 536/1 |
| 3,362,951 | 1/1968 | Farkas et al. | 536/1 |
| 3,822,250 | 7/1974 | Kimura et al. | 536/1 |
| 3,960,832 | 6/1976 | Kang et al. | 536/1 |

*Primary Examiner*—Johnnie R. Brown
*Attorney, Agent, or Firm*—Gabriel Lopez; Hesna J. Pfeiffer

[57] ABSTRACT

The new heteropolysaccharide S-130, prepared by fermentation of an unnamed *Alcaligenes* species, ATCC 31555 has valuable properties as a thickening, suspending and stabilizing agent in aqueous systems. It is especially useful in formulating oil well drilling fluids and muds. Its chemical composition is 2.8–7.5% acyl groups, 11.6–14.9% glucuronic acid; and the neutral sugars mannose, glucose and rhamnose, in the approximate molar ratio 1:2:2.

1 Claim, No Drawings

HETEROPOLYSACCHARIDE S-130

CROSS-REFERENCE

This is a continuation-in-part of U.S. Ser. No. 73,573 filed Sept. 7, 1979, now abandoned.

BACKGROUND OF THE INVENTION

Compound S-130 may be prepared by fermentation of a suitable nutrient medium with a hitherto undescribed organism, based on extensive taxonomic studies, which is an unnamed Alcaligenes species. An unrestricted permanent deposit of this organism employed in making our heteropolysaccharide was made with the American Type Culture Collection on Aug. 27, 1979 under Accession No. ATCC 31555.

The following considerations make the assignment of a new Alcaligenes species justified and necessary.

DESCRIPTION OF THE STRAIN

A. Characteristics of Colonial Morphology

On nutrient agar, small yellow colonies appear in one day at 30° C. with the diameter reaching about 1.5 mm after 5 days' incubation. The colonies are round, smooth, convex, mucoid, and opaque. The yellow color becomes more deep and the texture of colonies becomes hard after prolonged incubation.

On YM agar, small mucoid yellow colonies appear in one day and the diameter reaches about 3 mm after 5 days' incubation. The colonies are round, smooth, convex, and opaque, but the top of the colonies are flat. No membraneous hard texture is observed.

B. Characteristics of Cell Morphology

Strain S-130 is a gram-negative rod-shaped bacterium. On nutrient agar the average size of the cell is about 0.5–0.6 by 1.2–1.6 $\mu$m; ends of the cells are tapered and curvature was often seen. The size and shape of the cells do not change significantly after prolonged incubation.

On YM agar the average cell size is 0.6–0.8 by 1.6–2.0 $\mu$m, but the cell becomes longer (3–4 $\mu$m); accumulation of PHB is significant. Motility is positive. Flagella stains (modified silver nitrate method) show that the strain has mixed flagellation, i.e., polar and lateral flagella, as well as peritrichous flagella.

C. Physiological and Biochemical Characteristics

The following are results of tests employed:

Cytochrome oxidase is weak or negative; catalase positive.

Organism is capable of growth at 37° and 41° C., but not at 43° C.

Tolerance to 3.0% NaCl, but not to 6.5% NaCl.

Growth at pH between 5 and 12.

Aerobic acid but not gas was produced from various carbohydrates, such as:

| | |
|---|---|
| D-xylose | lactose |
| L-arabinose | maltose |
| D-glucose | melibiose |
| fructose | sucrose |
| galactose | trehalose |
| mannose | raffinose |

Litmus milk was reduced, but not peptonized.
ADH was positive, but not LDC, ODC, and PDA.
MR positive, but negative for VP, indole, and urease.
Esculin gelatin (weak) and Tween 80 (weak) were hydrolyzed, but not casein, starch, cellulose, pectin.

No phosphatase, and haemolysis negative.

0.1% triphenyltetrazolium chloride was not inhibitory.

Survival at 60° C. for 30 minutes.

Organisms grow on EMB agar and Tellurite Blood, but not on SS and MacConkey agar.

D. Antibiotic Susceptibility Test

The strain S-130 is susceptible to the following antibiotics:

| | |
|---|---|
| Kanamycin | 30 $\mu$g |
| Neomycin | 30 $\mu$g |
| Chlortetrcycline | 5 $\mu$g |
| Novobiocin | 30 $\mu$g |
| Erythromycin | 15 $\mu$g |
| Tetracycline | 30 $\mu$g |
| Gentamicin | 10 $\mu$g |
| Carbenicillin | 50 $\mu$g | and not susceptible to:

| | |
|---|---|
| Penicillin | 10 units |
| Streptomycin | 10 $\mu$g |
| Colistin | 10 $\mu$g |
| Polymyxin B | 300 units |

E. Nutritional Characteristics

Organic growth factors are not required and ammonium salts serve as the sole nitrogen source. A total of 30 organic compounds are utilized as sole source of carbon and energy. Most carbohydrates are utilized.

F. G+C Content of the DNA

No DNA analysis was performed.

G. Identification by API System

The strain could not be identified by this system.

H. Identification

The strain S-130 is a gram-negative aerobic rod-shaped organism. The mode of flagellation of the organism is mixed; polar and peritrichous flagella (possibly degenerate flagella) are seen. According to Bergey's Manual (8th Edition), such organisms belong as a member of the genus Alcaligenes.

TABLE 1

| Biochemical and Other Miscellaneous Tests Employed for the Strain S-130 | | | |
|---|---|---|---|
| Oxidase: Kovac's | + (weak) | Hydrolysis of: | |
| Pathotech | + (weak) | Gelatin | + (weak) |
| | | Casein | — |
| Catalase | + | Starch | — |
| OF medium: | | | |
| Oxidative | + | Tween 80 | + (weak) |
| Fermentative | — | Pectin | — |
| Gas from glucose | — | Alginate | NT |
| H$_2$S production: | — | Cellulose | — |
| TSI from cystine | ± | Chitin | — |
| Ammonium from peptone | NT | DNA | NT |
| β-Galactosidase (ONPG) | + | Esculin | + |
| Arginine dihydrolase | + | | |
| Lysine decarboxylase | — | Growth on various media: | |
| Ornithine decarboxylase | — | EMB agar | + |
| Tryptophan deaminase | NT | MacConkey agar | — |
| Phenylalanine deaminase | — | SS agar | — |
| Urease | — | Mannitol salt agar | — |

TABLE 1-continued

Biochemical and Other Miscellaneous Tests Employed for the Strain S-130

| | | | |
|---|---|---|---|
| Indole | − | TCBS agar | − |
| MR test | + | Tinsdale tellurite | |
| VP test | − | blood agar | + |
| Nitrate reduction | − | Pseudosel agar | NT |
| Nitrite reduction | − | | |
| Denitrification | NT | Pigment production: | |
| N₂-fixation: | | King A medium | − |
| Growth in Burk's medium | + | King B medium | − |
| Nitrogenase activity | NT | | |
| Malonate (oxidation) | − | Dye reaction: | |
| Phosphatase | − | Congo red | − |
| Haemolysis (sheep blood) | − | | |
| Litmus milk: acid, reduction only | | | |
| 3-ketolactose production | − | | |
| Survival at 60° C. for 30 min. | + | | |
| TSI: Slant | Acid | | |
| Butt | No growth | | |
| Gas | − | | |
| Egg Yolk Reaction | − | | |

+ = positive
− = negative
NT = not tested

FERMENTATION CONDITIONS

Heteropolysaccharide S-130 is produced during the aerobic fermentation of suitable aqueous nutrient media under controlled conditions via inoculation with the organism of the unnamed Alcaligenes species. The media contain sources of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 4% by weight of the medium. Preferably 3% glucose is used. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.05% to 0.4% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limitative.

As an alternative medium, S-130 may be grown under low $Ca^{++}$ conditions, i.e., in deionized water, or some other aqueous system substantially free of $Ca^{++}$ ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the Alcaligenes culture and producing the polysaccharide S-130 can vary from about 6 to 8, preferably 6.5 to 7.5.

Although the polysaccharide S-130 is produced by both surface and submerged culture, it is preferred to carry out the fermentation in the submerged state.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1–2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-130 is particularly suited for the preparation of large quantities.

The product is recovered from the fermentation medium by precipitation with a suitable alcohol, such as isopropanol.

HETEROPOLYSACCHARIDE S-130

The heteropolysaccharide produced by an unnamed Alcaligenes species is composed principally of carbohydrate with 2.8–7.5% (calculated as O-acetyl) O-acyl groups.

The carbohydrate portion of the S-130 polysaccharide contains 11.6–14.9% glucuronic acid and the neutral sugars mannose, glucose and rhamnose in the approximate molar ratio 1:2:2. The ratio of terminally linked rhamnose to 1,4 linked rhamnose is 1:2. The glucose is principally 1,3 linked.

The acetyl content of 5–10% was determined by treating a 0.2% aqueous solution of S-130 gum with an alkaline, hydroxylamine reagent followed by treatment with an acidic ferric chloride reagent [S. Hestrin (1949) J. Biol. Chem. 180 pp. 249–261].

The neutral sugars of polysaccharide S-130 were determined by dissolving ten mg. of the product in 2 ml 2 N $H_2SO_4$, and the mixture is heated at 100° C. for 4 hours. The resulting solution is cooled, neutralized with barium hydroxide and the pH is brought to 5–6 with solid carbon dioxide. The resulting precipitate of barium sulfate is removed by centrifugation and the supernatent is concentrated to a syrup under reduced pressure. The sugars in the hydrolysate are tentatively identified by gas-liquid chromatography of their aldononitrile acetate derivatives on a Hewlett-Packard Model 5750 chromatograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) *Carbohydr. Res.* 27 pp. 464–467].

The various neutral sugars of the polysaccharides were also characterized by use of descending paper chromatography on Whatman No. 1 chromatography paper using as the solvent the upper layer of pyridine:ethyl acetate:water (2:5:5). Chromatograms were stained using silver nitrate dip and acid analine phthalate spray reagent. Component sugars were identified by co-chromatography with sugar standards and by the specific-color reaction with the analine phthalate reagent.

The glucuronic acid content of the polysaccharide was determined by decarboxylation with 19% hydrochloric acid and the liberated carbon dioxide was trapped in standard sodium hydroxide and determined by back titration [B. L. Browning (1967) *Methods of Wood Chemistry* II, pp. 632–633].

Paper electrophoresis was used for the separation and tentative identification of the glucuronic acid present in the neutralized acid hydrolysate described above. Aliquots of this and known glucuronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the glucuronic acids being separated.

The polysaccharide S-130 imparts viscosity to an aqueous medium when dissolved in water in low concentrations. Because of this, its sensitivity to shear and overall rheology, it is useful as a thickening, suspending, emulsifying, stabilizing, lubricating, film-forming, or binding agent, especially in aqueous systems. In particular, it has uses in the following applications or products: adhesives, wall-joint cements, water-retentive grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrated and flowable pesticides and herbicides, tobacco binders, water-based inks lithographic fountain solutions, leather finishes, hydro-mulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressings, dry mixes, icings, and glazes, syrups, puddings, farinaceous foods, canned and retorted foods, and bakery fillings.

A particularly valuable utility is in the field of petroleum and water-well drilling muds. More detailed examples illustrating this preferred use are found, *infra*.

Although S-130 gum possesses a general viscosity-imparting property, its particular profile of solution properties is a distinctive characteristic which enables it to be distinguished over other heteropolysaccharides.

Briefly, the gum is high viscosity in the presence of 0.1% KCl (1650 cPs) and DI water (1470 cPs). It shows excellent acetic acid heat stability (+36%) and heat stability (−1%). A gel is formed in the presence of heat and 1% NaOH. This gum is KCl-reactive showing a greater than 16% viscosity increase in the presence of 0.1% and 2.5% KCl. A brittle, low tensile strength film is formed.

The gum's properties of good viscosity in brine (KCl and NaCl), and seawater, good acid and heat stability, a constant viscosity over pH ranges 1.5 to 12.1, and good shear stability, make it especially suitable for industrial applications such as drilling and petroleum applications fluid. Specifically, S-130 gum has excellent heat stability, and no viscosity loss occurs upon autoclaving at 121° C. and 150 psi for 15–20 minutes.

1. Viscosity and Shear
   A. Brookfield

|   |   | DI $H_2O$ | DI $H_2O$ + 0.1% KCl |
|---|---|---|---|
| 1. | 1.0% @ 60 rpm | 1470 cPs | 1650 cPs |
|    | @ 6 rpm | 10,400 cPs |  |
|    | Spindle No. 3 |  |  |
| 2. | 0.1% (UL adapter)[a] | 45 cPs | 30 cPs |
| 3. | 0.5% Wells-Brookfield |  |  |
|    | @ 9.6 sec$^{-1}$ | 680 cPs | 1180 cPs |

B. Shear[b]
   1. n @ 19.2 sec$^{-1}$     10,110 cPs
   2. n @ 9.6 sec$^{-1}$      2200 cPs
   3. n @ 76.8 sec$^{-1}$     320 cPs
   4. n @ 384 sec$^{-1}$      60 cPs
   5. n @ $384^2$ sec$^{-1}$  60 cPs
   6. n @ 9.6 sec$^{-1}$      1800 cPs C. 40° F. Storage:
      2050 cPs @ 60 rpm, with spindle No. 4, very chunky flow, increase of 39% viscosity over ambient temperature viscosity.

2. Acid, Base, Heat Stability
   A. Stability
      1. Acetic acid plus heat
         initial n: 2500 cPs
         final n: 3600 cPs
         % change: +36
      2. 1% HCl plus heat
         initial n: 1230 cPs
         final n: total loss
         % change: total loss
      3. 1% NaOH plus heat
         initial n: 1380 cPs
         final n: Gel
         % change: Gel
      4. Heat only
         initial n: 2130 cPs
         final n: 2100 cPs
         % change: −1

B. pH Effect
      1. 5% acetic acid     2.71 pH    2560 cPs[c]
      2. 5% $NH_4OH$        11.09 pH   2070 cPs[c]

3. and Dye Compatibility
   A. Salt
      1. $CaCl_2$ (saturated)                compatible -continued

| | | |
|---|---|---|
| 2. Amm. polyphosphate | | precipitate |
| 3. 60% NH$_4$NO$_3$ | | compatible |
| 4. 1% Al$_2$(SO$_4$)$_3$.18H$_2$O | | compatible |
| 5. 1% CaCl$_2$.2H$_2$O | | compatible |
| 6. 1% KCl | | compatible |
| 7. 0.1% KCl | | 2560 cPs[c] |
| 8. 2.5% KCl | | 2560 cPs[c] |
| B. Dyes | | |
| 1. Milling Green | | compatible |
| 2. Methylene Blue | | precipitate |

4. Texture/Flow Properties

High viscosity gum, chunky flow, no gelation, gummy to the touch.

5. Synergism and Enzymes[c]

| | 1% n | 0 hr of mixture | 2 hr n of mixture |
|---|---|---|---|
| A. Guar | 2320 cPs | 2560 cPs | 2560 cPs |
| B. H.P. Guar | 1960 cPs | 1950 cPs | 2560 cPs |
| C. CMC | 870 cPs | 1310 cPs | 970 cPs |
| D. HEC | 440 cPs | 870 cPs | 1180 cPs |
| E. SMS 47-6 | 2130 cPs | | |

| | Expected viscosity | Synergism |
|---|---|---|
| A. Guar | 2230 cPs | +15% |
| B. H.P. Guar | 2050 cPs | +25% |
| C. CMC | 1360 cPs | None % |
| D. HEC | 970 cPs | +22% |

6. Milk Reactivity

A. Dispersion: Excellent
B. Whey off: 1st day
C. Other observations:

7. Film Formation

Uneven pull down; film formed, not plastic, very brittle, low tensile strength.

[a]Viscosity measured on a Brookfield Model LVF at 6 rpm with the No. 1 spindle and a UL adapter.
[b]All measurements made on a Wells-Brookfield microviscometer Model RVT-c/p.
[c]Viscosity measured on a Wells-Brookfield microviscometer Model RVT-c/p at 9.6 sec$^{-1}$.

EXAMPLE 1

Fermentation Procedure for Producing Heteropolysaccharide S-130

A. Culture Maintenance

The unnamed Alcaligenes organism, ATCC 31555, grows quite well on NA agar, with good colonial morphology. The incubation temperature is 30° C. The organism produces a yellow pigment.

B. Seed Preparation

Flask seeds are prepared in YM broth incubated at 30° C. for 24 hours, then used to inoculate seed medium which is the same as final fermentor medium. A 5% inoculum is used for a 14 L fermentor.

C. Final Fermentor Medium

The following medium gives acceptable results in the 14 L fermentor and can be used for larger scale 20 L and 70 L fermentors:

| | |
|---|---|
| Glucose | 3.0% |
| K$_2$HPO$_4$ | 0.05% |
| Promosoy | 0.05% |
| NH$_4$NO$_3$ | 0.09% |
| MgSO$_4$.7H$_2$O | 0.01% |
| Fe$^{++}$ | 1 ppm |
| HoLe salts | 1 ml/L |

The pH is controlled between 6.5 and 7.5. At 0 hours, pH is 7.3 and residual carbon source was measured to be 3.07%. After 25.5 hours, pH was 7.0 and beer viscosity measured 2350. After 63.5 hours, pH was 6.3 and beer viscosity 3950, and the reaction is terminated by adding 4% isopropanol.

HoLe salts are a trace element solution containing tartrate, magnesium molybdate, CoCl$_3$, ZnCl$_2$, CuCl$_2$, boric acid, manganese chloride and ferrous sulfate.

The initial agitation and aeration rates were 400 rpm and 3 L/M, respectively. The aeration remained constant throughout the fermentation. The agitation was increased as necessary during the fermentation to ensure good mixing. Maximum agitation was 1600 rpm.

When a low calcium product is desired, the medium above is used with deionized water.

D. Recovery

Fermentation beer is pasteurized at 167° F. for 10–15 minutes. Good fibers are produced under precipitation conditions giving 58–60% spent IPA.

E. Drying

Product is recovered after drying at 50°–55° C. for about one hour in a forced-air tray dryer.

The product prepared in this example shows a 1% viscosity of 1490 in deionized water, and 2400 at 1% in DI water containing 1% added KCl. It analyzed 12% glucuronic acid; 28% glucose; 13% mannose; 59% rhamnose; 3.5% acetyl, and no pyruvate.

Measurements of this gum is 2% KCl show excellent viscosity development, with excellent NaCl stability and maintenance of viscosity up to at least 300° F.; slight gelation of gum is observed in 2% KCl.

EXAMPLE 2

Sea Water Mud Composition

S-130 has utility in muds used for oil well drilling. A formula and data for a sea water mud are as follows:

| S-130 | | | 1.0 lb | | |
|---|---|---|---|---|---|
| Sea water | | | 1.0 bbl | | |
| Fann viscosity data: | | | | | |
| Speed (rpm) | 3 | 6 | 100 | 200 | 300 | 600 |
| Dial Reading | 3.4 | 3.8 | 8.5 | 11.0 | 13.2 | 17.2 |
| pH = 7.1 | | | | | | |

EXAMPLE 3

Hydraulic Fracturing Fluid Composition

Hydraulic fracturing fluid example—for high temperatures (over 200° F.):

| per 1000 gallons: | | | | | |
|---|---|---|---|---|---|
| H$_2$O | | | | | |
| 5% Methanol or 500 ppm sodium sulfite | | | | | |
| 2% KCl | | | | | 165 lb |
| Ammonium persulfate | | | | | 10 lb |
| S-130 | | | | | 40 lb |
| Viscosity of the above fluid: | | | | | |
| Fann 35 rpm | 600 | 300 | 200 | 100 | 6 | 3 |
| Viscosity, cP | 15.0 | 24,2 | 33.4 | 53.3 | 450 | 813 |

EXAMPLE 4

S-130 Fermentation Procedure

A. Culture Maintenance

The unnamed Alcaligenes organism, ATCC 31555 grows quite well on nutrient agar. The incubation temperature is 30° C. The organism produces a yellow pigment.

B. Seed Preparation

Flask seeds are prepared in YM broth incubated at 30° C. for 24 hours with shaking. Fresh YM broth seeds are then started using a 1% inoculum. After 24 hours incubation at 30° C. with shaking these YM seeds are used to inoculate a one-gallon fermentor containing a seed medium which is the same as the final fermentor medium except that it contains 0.5% $K_2HPO_4$. The inoculum size is 6.7% and the fermentation temperature is 30° C. The air flow rate is one L/M and the agitation is set at 400 RPM. At 25 hours this seed was used to start a 30 L fermentor with an inoculum size of 5%.

C. Final Fermentor Medium

The following medium gives acceptable results in the 30 L fermentor and can be used for larger scale fermentors such as 70 L.

| | |
|---|---|
| Glucose | 3.0% |
| $K_2HPO_4$ | 0.05% |
| Promosoy | 0.50% |
| $NH_4NO_3$ | 0.01% |
| $MgSO_4.7H_2O$ | 0.047% |
| $Fe^{++}$ | 1 ppm |
| HoLe Salts | 1 ml/L |
| Defoamer (Balab) | 0.03% |
| Defoamer (Proflo Oil) | 0.10% |

The pH is controlled between 6.5 and 7.5. At 0 hours, the residual carbon source was measured to be 3.08%. At 69 hours the pH was 6.55 and the beer viscosity was 42,500 cP.

HoLe salts are a trace element solution containing tartrate, magnesium molybdate, $CoCl_3$, $ZnCl_2$, $CuCL_2$, boric acid, manganese chloride and ferrous sulfate.

The initial agitation and aeration rates were 300 RPM and 5 L/M, respectively. The aeration rate was increased to 10 L/M at 20 hours and then remained constant throughout the fermentation. The agitation was increased to 700 RPM (maximum) at 20 hours.

When a low calcium product is desired, the medium above is used with deionized water.

D. Recovery

Fermentation beer is pasteurized at 167° F. for 10-15 minutes. Good fibers are produced under precipitation conditions giving 58-60% spent IPA.

E. Drying

Product is recovered after drying at 50°-55° C. for about one hour in a forced air tray dryer.

The product prepared in this example shows a 1% viscosity of 1350 cps in deionized water and 1440 cps in deionized water containing 1% added KCl. It analyzed 13.2% glucuronic acid; 38% glucose; 18% mannose; 38% rhamnose; 2.5% acetyl and no pyruvate.

This product has been demonstrated to have thermal and solution properties similar to the sample described in the Example 1.

EXAMPLE 5

Methylation Analysis

Samples of S-130 have shown analyses indicated on Table II. A partial structural determination was performed by methylation of the component sugars. The methylated sugars were separated by gas chromatography, and then analyzed on a mass spectrometer. This analysis demonstrated that the ratio of thermally linked to 1,4 linked rhamnose sugars is 1:2 and that the glucose is primarily 1,3 linked.

TABLE II

| Composition S-130 | | | | | | | |
|---|---|---|---|---|---|---|---|
| GluA (%) | Neutral Sugars[1] | | | | | Pyruvic Acid (%) | O—Acyl[2] (%) |
| | Glu | Man | Rha | Rib | Ara | | |
| 11.6-14.9 | 26-46 | 17-20 | 33-37 | — | tr | 0 | 2.8-7.5 |

[1] % of total neutral sugars
[2] Calculated as O—Acetyl

Approximately 40 mg dialyzed and freeze dried sample of S-130 was weighed (dry) into 100 ml serum bottles before inserting rubber serum caps. Then approximately 40 ml of dimethyl sulfoxide (DMSO) (redistilled and dried over 4 A molecular sieves) was added. The sample was dissolved by heating in a sonic bath for ca. 20 hr. at ca. 50° C. while the vial was continuously flushed with dry nitrogen. To the vial was added 20 ml anion solution made from DMSO and NaH (2.5 g/50 ml DMSO). The vial was placed in sonic water bath for ca. 30 min. before leaving at room temperature overnight. The solution was cooled and then 20 ml $CH_3I$ was added via a syringe. After stirring for at least one hour, the excess $CH_3I$ was rotovaped off before dialysis (DI water) and concentrating to dryness (rotovap).

Hydrolysis of methylated gums and derivatation of methyl sugars

The sample was hydrolyzed by a two-step procedure using 90% formic acid/0.13 M $H_2SO_4$. The resulting sugars were reduced with $NaBH_4$ and the resulting alditols were acetylated with acetic anhydride/pyridine (1:1) at 100° C.

Gas Chromatography

The methyl sugars, as their alditol acetates, were separated by gas chromatography using either SP-2330 or OV-225 columns. The following conditions were used:

3% SP-2330 (on 100/120 Supelcoport, 2 mm×6 ft)

| | |
|---|---|
| Column temp. | isothermal at 190° C. |
| Injection port | 215° C. |
| FID Temp | 350° C. |
| Oven Max | 250° C. |
| Chart Speed | 0.50 |
| Attenuation | 8 |
| FID Signal | A-B |
| Slope Sensitivity | 0.50 |
| Area Rejection | 1 |
| Flow A | 40 |
| Flow B | 40 |

3% OV-225 (on 80/100 Supelcoport, 2 mm×4 ft)
Column temp—isothermal at 170° C.
(other conditions as above)

The same columns and flow rates were used with GC/Mass Spectrometer. The retention times (RT) on the Hewlett Packard Model 5830 A gas chromatograph were found to be much more reproducible than on the Hewlett Packard Model 5992 A GC/Mass spectrometer. The identities were deduced by looking at both RT's and mass fragmentation patterns. With the columns used it is not possible to determine if the 2,6 $Me_2$ hexose found in S-130 is 2,6 $Me_2$ glucose or 2,6 $Me_2$ mannose. Based on the relative amounts of glucose and mannose expected from alditol acetate analysis of neutral sugars and based on the amounts of other methyl sugars found (Table III), S-130 probably contains 2,6 Me$_2$ mannose. However, these data are shown in Table III as 2,6 Glucose/Mannose.

Based on the methylation data, the amounts of the various linkages are shown in Table IV.

TABLE III

Relative Amounts of Methyl Sugars

| | S-130 (Wt. %) | Linkage |
|---|---|---|
| 2,3,4 Me$_3$ Rha | 17.4 | Terminal |
| 2,3 Me$_2$ Rha | 41.2 | 1,4 |
| 2,4,6 Me$_3$ Glu | 19.6 | 1,3 |
| 2,3,6 Me$_3$ Glu | 3.0 | 1,4 |
| 2,3,6 Me$_3$ Man | — | 1,4 |
| 2,6 Me$_2$ Glu/Man | 18.9 | 1,3,4 |

TABLE IV

Types and Amounts of GLYCOSIDIC LINKAGES

| Linkage | Moles |
|---|---|
| Term. Rha | 1 |
| 1,4 Rha | 2 |
| 1,3 Glu | 1 |
| 1,4 Man | — |
| 1,3,4 Glu/Man | 1 |

What is claimed is:

1. Heteropolysaccharide S-130, which is principally carbohydrate, comprising 2.8–7.5% (calculated as O-acetyl) O-acyl groups, 11.6–14.9% glucuronic acid, and the neutral sugars mannose, glucose, and rhamnose in the approximate molar ratio 1:2:2, wherein the ratio of terminally linked rhamnose to 1,4 linked rhamnose is 1:2 and the glucose is primarily 1,3 linked.

* * * * *